United States Patent [19]

Honma

[11] Patent Number: 4,838,880
[45] Date of Patent: Jun. 13, 1989

[54] PLASTIC INSERTER
[75] Inventor: Masaaki Honma, Yokohama, Japan
[73] Assignee: Nifco, Inc., Yokohama, Japan
[21] Appl. No.: 87,585
[22] Filed: Aug. 20, 1987
[30] Foreign Application Priority Data Aug. 22, 1986 [JP] Japan .................................. 61-127228

[51] Int. Cl.⁴ .............................................. A61M 5/00
[52] U.S. Cl. ........................... 604/280; 128/DIG. 26; 24/499; 24/545
[58] Field of Search ............... 604/280, 171, 178, 177, 604/174, 159; 128/303, 321, 322, 346, DIG. 26; 24/487, 499, 513, 535, 545, 546, 547

[56]  References Cited
U.S. PATENT DOCUMENTS

| 3,030,681 | 4/1962 | Philips | 24/499 X |
|---|---|---|---|
| 3,446,211 | 5/1969 | Markham | 128/322 |
| 3,782,383 | 1/1974 | Thompson et al. | 24/545 X |
| 3,814,080 | 6/1974 | Norman | 604/174 |
| 4,079,765 | 3/1978 | Hatayan | 24/545 X |
| 4,484,911 | 11/1984 | Berlin et al. | 128/DIG. 26 X |

Primary Examiner—Stephen C. Pellegrino
Attorney, Agent, or Firm—Schwartz & Weinrieb

[57] ABSTRACT

A plastic inserter comprises movable and stationary jaws openably and closably connected together by means of a thin hinge, a space formed between the movable and stationary jaws along the hinge so that a flexible hollow tube is allowed to pass therethrough, a handle plate including an elastic supporting piece integrally formed with a part of the stationary jaw, and handle piece integrally formed with the movable jaw and adapted to hold the movable jaw in a shut state with respect to the stationary jaw when engaged with the elastic supporting piece of the stationary jaw.

20 Claims, 2 Drawing Sheets

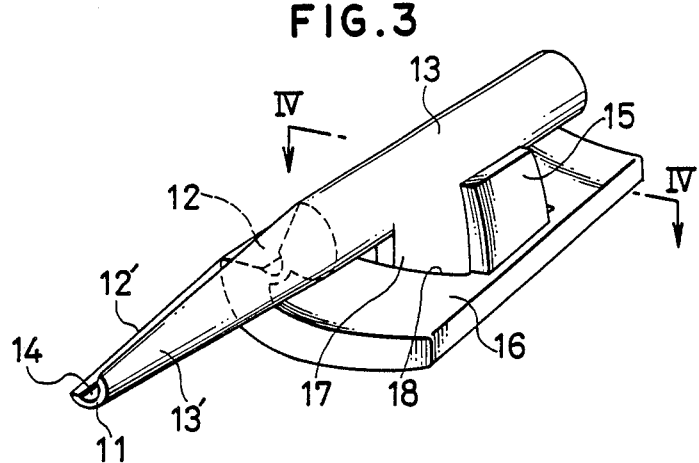
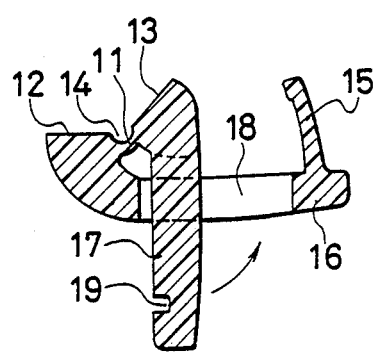
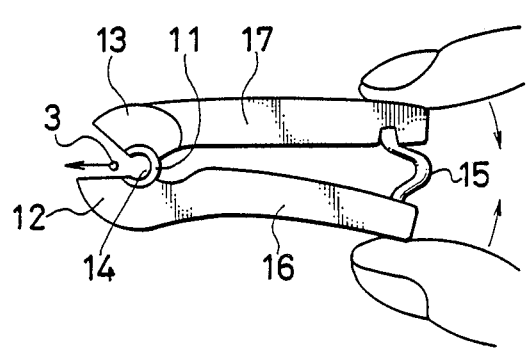
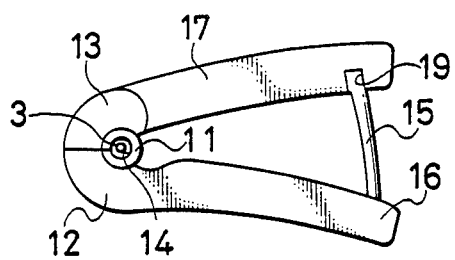

PLASTIC INSERTER

BACKGROUND OF THE INVENTION

1. Field of the Invention

This invention relates to an inserter for use in a fluid therapy system for a clinical catheter introduction kit or the like for inserting an elongated flexible hollow tube of small diameter into a small cup-like housing mounted upon the upper end a thin tube.

2. Description of the Prior Art

The conventional inserter, as is shown in FIG. 1, is a hollow cylindrical body 1. One end of the inserter is converged or tapered. The inserter is passed through a thin tube 4 having a cup-like housing 2 mounted upon the upper end thereof by inserting the tapered end of the inserter into the cup-like housing 2 and then passing an elongated flexible hollow tube 3 having a small diameter therethrough.

In order to pass the flexible hollow tube 3 through a thin tube 4, the flexible hollow tube 3 must initially be axially inserted into the inserter 1 from its front end. After the flexible hollow tube 3 has been inserted into the thin tube 4 by means of a predetermined depth, the inserter 1 must be removed therefrom. In this case, the inserter must be axially withdrawn up to the other end of the flexible hollow tube 3 and then removed. Accordingly, much time and labor is required. In addition, the work efficiency is poor.

OBJECT OF THE INVENTION

A general object of the present invention is to provide an inserter, in which a flexible hollow tube can be removed at a desired position, and which is excellent in work efficiency and is economical to produce.

SUMMARY OF THE INVENTION

To achieve the above-mentioned object, according to the present invention, there is essentially provided an inserter comprising movable and stationary jaws openably and closably connected together by means of a thin hinge, a spacing means formed between the movable and stationary jaws along the hinge so that a flexible hollow tube is allowed to pass therethrough, a handle plate including an elastic supporting piece integrally formed with a part of the stationary jaw, and a handle piece integrally formed with the movable jaw and adapted to hold the movable jaw in a shut state with respect to the statonary jaw when engaged with the elastic supporting piece.

In the above-mentioned inserter, the handle piece of the movable jaw is normally biased by means of the elastic supporting piece of the stationary jaw, the movable jaw is shut with respect to the stationary jaw, and the space along the hinge holds the flexible hollow tube therein without allowing the tube to escape therefrom and axially guides the flexible hollow tube so as to be passed into the thin tube. When the flexible hollow tube has been inserted into the thin tube by means of a predetermined depth, the handle piece of the movable jaw and the handle plate of the stationary jaw are squeezed together by means of the fingers. When the squeezing force of the fingers is increased, the movable jaw is opened with respect to the stationary jaw. Simultaneously, the space along the hinge is also opened. As a result, the flexible hollow tube held within the space is released.

In this way, the inserter according to the present invention has the advantage in that when the flexible hollow tube is to be removed, the flexible hollow tube is not required to be withdrawn toward the end portion thereof as in the conventional case and can be easily removed at any desired position thereof. Thus, the work efficiency is greatly increased.

BRIEF DESCRIPTION OF THE DRAWINGS

The above and other objects and features of the invention will become more apparent from the following detailed description with reference to the accompanying drawings wherein:

FIG. 3 is a perspective view of a molded inserter;

FIG. 4 is a sectional view taken along line IV—IV of FIG. 3;

FIG. 5 is a side view of an inserter with its jaws opened; and

FIG. 6 is a side view of an inserter with its jaws shut.

DETAILED DESCRIPTION OF THE PREFERRED EMBODIMENT

Figure 1:
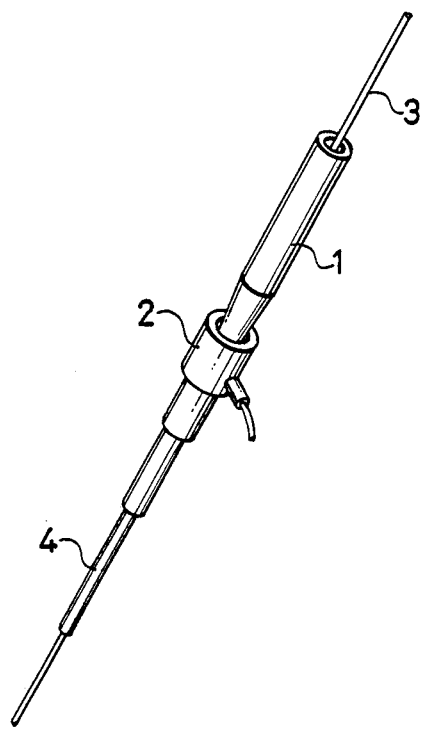
FIG. 1 is a perspective view of a conventional inserter in use.
Figure 2:
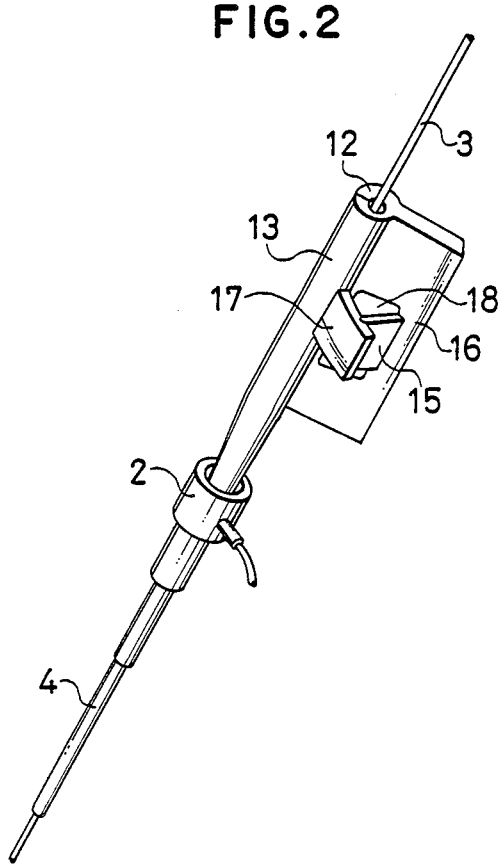
FIG. 2 is a perspective view of an inserter according to the present invention in use.

The accompanying drawings illustrate one embodiment of an inserter according to the present invention, in which reference numeral 11 denotes a thin hinge, and 12 and 13 denote stationary and movable jaws which are openably and closably connected together by means of the hinge 11. These members are integrally molded of a plastic material such as, for example, polypropylene.

Between the pair of jaws 12 and 13, a generally C-shaped space 14 is defined along the hinge 11 in order to allow a flexible hollow tube 3 to pass therethrough. Half portions 12' and 13' of the pair of jaws 12 and 13 become gradually narrower in external configuration and are thus easy to be inserted into a cup-shaped housing 2.

A handle plate 16 having an elastic supporting piece 15, and a handle piece 17 are integrally provided upon the other half portions of the stationary and movable jaws 12 and 13 with. In order to shut the movable jaw 13 respect to the stationary jaw 13 by engaging the elastic supporting piece 15 of the handle plate 16 against the handle piece 17, the handle plate 16 of the stationary jaw 12 is formed with a window hole 18. The handle piece 17 of the movable jaw 13 is formed such that it can pass through the window hole 18 in a downwardly direction as seen in FIG. 4.

FIGS. 3 and 4 illustrate the pair of jaws 12 and 13 connected together by means of the hinge 11 and molded in the manner as described. The elastic supporting piece 15 projects upwardly from the edge of the window hole 18.

As is shown in FIG. 4, the pivotably jaw 13 is pivoted about the hinge 11 so as to raise the handle piece 17 upwardly out of the window hole 18, and the rear end of the handle piece 17 is engaged with the upper end of the elastic supporting piece 15. Due to the foregoing, the movable jaw 13 is held in its shut state with respect to the stationary jaw 12 by means of the elastic supporting piece 15.

When the handle piece 17 is being raised upwardly from the window hole 18, the handle piece 17 encounters the elastic supporting piece 15. However, since the elastic supporting piece 15 has flexibility, the handle piece 17 can be raised upwardly from the window hole 18 without any difficulty.

Preferably, the rear end portion of the handle piece 17 is provided with a suitable engaging portion 19 such as a groove for housing the upper end portion of the elastic supporting piece 15 as illustrated, so that it will not be disengaged.

Due to the foregoing, when the handle plate 16 and the handle piece 17 are firmly together by means of the fingers, the elastic supporting piece 15 is bent and the pair of jaws 12 and 13 are opened as shown in FIG. 5, the flexible hollow tube 3 can be inserted into the space 14 formed along the hinge 11 so as to pass into the thin tube 4, or the inserter can be easily removed from the flexible hollow tube when the flexible hollow tube 3 has been inserted into the thin tube 4 by means of a predetermined depth.

Since, as shown in FIG. 6, the space 14 is normally shut by means of the pair of jaws 12 and 13, the flexible hollow tube 3 can be firmly held and guided into the thin tube 4 as a result of being accommodated within the space 14.

According to the present invention, there can be provided an inserter in which a space for holding and guiding a flexible hollow tube can be opened and closed by means of a pair of jaws and thereby, the flexible hollow tube can be firmly held and the inserter can be very easily removed from an axially intermediate portion of the flexible hollow tube.

Obviously, many modifications and variations of the present invention are possible in light of the above teachings. It is therefore to be understood that within the scope of the appended claims, the present invention may be practiced otherwise than as specifically described herein.

What is claimed is:

1. A gripping device, comprising:
a first jaw means for gripping an elongated member;
second jaw means movable with respect to said first jaw means between open and closed positions for permitting entry of said elongated member between said first and second jaw means, or removal of said elongated member from said first and second jaw means, when said first and second jaw means are relatively open, and for gripping said elongated member in a cooperative manner with said first jaw means when said first and second jaw means are relatively closed;
first handle means operatively connected to said first jaw means;
second handle means operatively connected to said second jaw means for cooperating with said first handle means such that when said first and second handle means are moved toward each other said first and second jaw means are relatively open, while when said first and second handle means are moved away from each other, said first and second jaw means are relatively closed with respect to each other;
cylindrical cavity means, defining a cylindrical cavity having a longitudinal axis along which said elongated member is housingly disposed when gripped by said first and second jaw means, for hingedly connecting said first and second jaw means together so as to permit said relative open and closed movements to occur about a hinge axis which is substantially parallel to said longitudinal axis of said cylindrical cavity,
wherein one of said first and second handle means is provided with means for biasing said first and second handle means apart so as to in turn bias said first and second jaw means together; and
the other one of said first and second handle means is provided with groove means for detachably receiving an end portion of said biasing means whereby said first and second handle means may be detachably connected together in a biased condition.

2. A gripping device as set forth in claim 1, wherein:
said first and second jaw means, said first and second handle means, and said cylindrical cavity means are all fabricated from molded plastic material.

3. A gripping device as set forth in claim 2, wherein:
said plastic material is polypropylene.

4. A gripping device as set forth in claim 1, wherein:
said biasing means comprises a flexible elastic member interposed between said first and second handle means.

5. A gripping device, comprising:
first jaw means for gripping an elongated member;
second jaw means movable with respect to said first jaw means between open and closed positions for permitting entry of said elongated member between said first and second jaw means, or removal of said elongated member from said first and second jaw means, when said first and second jaw means are relatively open, and for gripping said elongated member in cooperation with said first jaw means when said first and second jaw means are relatively closed;
first handle means operatively connected to said first jaw means;
second handle means operatively connected to said second jaw means for cooperating with said first handle means such that when said first and second handle means are moved toward each other said first and second jaw means are relatively open, while when said first and second handle means are moved away from each other, said first and second jaw means are relatively closed with respect to each other;
said first and second jaw means defining first and second portions of a cylindrical cavity having a longitudinal axis along which said elongated member is housingly disposed when gripped by said first and second jaw means; and
hinge means, defining a third portion of said cylindrical cavity, for hingedly interconnecting said first and second jaw means so as to permit said relatively open and closed movements of said first and second jaw means to occur about a hinge axis which is incorporated within said third cylindrical cavity defining portion and which is disposed substantially parallel to said longitudinal axis of said cylindrical cavity;
each of said first and second jaw means including a half section, in the circumferential direction of said cylindrical cavity, which is tapered in the direction of said longitudinal axis of said cylindrical cavity.

6. A gripping device as set forth in claim 5, wherein:
said first and second jaw means, and said hinge means, are all fabricated from molded plastic material.

7. A gripping device as set forth in claim 6, wherein:
said plastic material comprises polypropylene.

8. A gripping device as set forth in claim 5, further comprising:
first handle means operatively connected to said first jaw means; and
second handle means operatively connected to said second jaw means for cooperating with said first handle means such that when said first and second handle means are moved toward each other, said first and second jaw means are relatively open, while when said first and second handle means are moved away from each other, said first and second jaw means are relatively closed with respect to each other.

9. A gripping device as set forth in claim 3, wherein:
said first and second jaw means, said first and second handle means, and said hinge means, are all fabricated from molded plastic material.

10. A gripping device as set forth in claim 9, wherein: said plastic material is polypropylene.

11. A gripping device as set forth in claim 8, wherein:
one of said first and second handle means is provided with means for biasing said first and second handle means away from each other so as to in turn bias said first and second jaw means together; and
the other one of said first and second handle means is provided with means for engaging said biasing means whereby said first and second handle means are connected together in a biased condition.

12. A gripping device as set forth in claim 11, wherein:
said biasing means comprises a flexible elastic member interposed between said first and second handle means.

13. A gripping device as set forth in claim 6, wherein:
said first and second jaw means, and said hinge means are all fabricated from molded plastic material.

14. A gripping device as set forth in claim 13, wherein:
said plastic material is polypropylene.

15. A gripping device, comprising:
first jaw means for defining a first wall portion of a cylindrical cavity having a longitudinal axis;
second jaw means for defining a second wall portion of said cylindrical cavity and movable with respect to said first jaw means between open and closed positions for permitting entry of an elongated member between said first and second jaw means, or removal of said elongated member from said first and second jaw means, when said first and second jaw means are relatively open, and for gripping said elongated member in cooperation with said first jaw means when said first and second jaw means are relatively closed;
first handle means operatively connected to said first jaw means;
second handle means operatively connected to said second jaw means for cooperating with said first handle means such that when said first and second handle means are moved toward each other said first and second jaw means are relatively open, while when said first and second handle means are moved away from each other, said first and second jaw means are relatively closed with respect to each other; and
hinge means, integrally formed with said first and second jaw means as a single unit and defining a third wall portion of said cylindrical cavity within which said elongated member is disposed when said first and second jaw means are relatively closed, for hingedly interconnecting said first and second jaw means together so as to permit said relatively open and closed movements of said first and second jaw means to occur about a hinge axis which is incorporated within said third wall portion of said cylindrical cavity so as to extend substantially parallel to said longitudinal axis of said cylindrical cavity along which said elongated member is disposed when gripped by said first and second jaw means;
each of said first and second jaw means including a half section, in the circumferential direction of said cylindrical cavity, which is tapered in the direction of said longitudinal axis of said cylindrical cavity.

16. A gripping device as set forth in claim 15, further comprising:
first handle means operatively connected to said first jaw means; and
second handle means operatively connected to said second jaw means for cooperating with said first handle means such that when said first and second handle means are moved toward each other, said first and second jaw means are relatively open, while when said first and second handle means are moved away from each other, said first and second jaw means are relatively closed with respect to each other.

17. A gripping device, comprising:
first jaw means for gripping an elongated member;
second jaw means movable with respect to said first jaw means between open and closed positions for permitting entry of said elongated member between said first and second jaw means, or removal of said elongated member from said first and second jaw means, when said first and second jaw means are relatively open, and for gripping said elongated member in a cooperative manner with said first jaw means when said first and second jaw means are relatively closed;
first handle means operatively connected to said first jaw means;
second handle means operatively connected to said second jaw means for cooperating with said first handle means such that when said first and second handle means are moved toward each other, said first and second jaw means are relatively open, while when said first and second handle means are moved away from each other, said first and second jaw means are relatively closed with respect to each other;
cylindrical cavity means, defining a cylindrical cavity having a longitudinal axis along which said elongated member is housingly disposed when gripped by said first and second jaw means, for hingedly connecting said first and second jaw means together so as to permit said relative open and closed movements to occur about a hinge axis which is substantially parallel to said longitudinal axis of said cylindrical cavity; and
wherein one of said first and second handle means is provided with a window through which a free end of said other one of said first and second handle means can be moved about said hinge axis in order to maintain said first and second jaw means in a relatively open state.

18. A gripping device as set forth in claim 17, wherein:

said first and second jaw means, and said hinge means, are all fabricated from molded plastic material.

19. A gripping device as set forth in claim 18, wherein:

said plastic material is polypropylene.

20. A gripping device as set forth in claim 17, wherein:

one of said first and second handle means is provided with a flexible elastic biasing member interposed between said first and second handle means for biasing said first and second handle means apart so as to in turn bias said first and second jaw means together; and the other one of said first and second handle means is provided with groove means for detachably receiving an end portion of said biasing member whereby said first and second handle means may be detachably connected together in a biased condition.

* * * * *